United States Patent
Takeda et al.

(10) Patent No.: US 8,904,755 B2
(45) Date of Patent: Dec. 9, 2014

(54) HEATER CONTROL DEVICE OF OXYGEN CONCENTRATION SENSOR

(75) Inventors: Keiichi Takeda, Saitama (JP); Ken Noguchi, Saitama (JP)

(73) Assignee: Bosch Corporation, Tokyo (JP)

( * ) Notice: Subject to any disclaimer, the term of this patent is extended or adjusted under 35 U.S.C. 154(b) by 0 days.

(21) Appl. No.: 14/123,332

(22) PCT Filed: Mar. 29, 2012

(86) PCT No.: PCT/JP2012/058317
§ 371 (c)(1),
(2), (4) Date: Dec. 2, 2013

(87) PCT Pub. No.: WO2012/165019
PCT Pub. Date: Dec. 6, 2012

(65) Prior Publication Data
US 2014/0090363 A1   Apr. 3, 2014

(30) Foreign Application Priority Data
Jun. 2, 2011 (JP) .................................. 2011-124306

(51) Int. Cl.
| | |
|---|---|
| *F01N 3/00* | (2006.01) |
| *F01N 11/00* | (2006.01) |
| *F02D 41/14* | (2006.01) |
| *F02N 11/08* | (2006.01) |
| *G01N 27/406* | (2006.01) |

(52) U.S. Cl.
CPC .......... *F01N 11/007* (2013.01); *F02D 41/1494* (2013.01); *F02N 11/0814* (2013.01); *G01N 27/4067* (2013.01); *F02D 41/1454* (2013.01); *Y02T 10/48* (2013.01)
USPC ................... 60/276; 60/284; 60/285; 60/286; 60/300; 73/114.72; 73/114.73; 73/114.75

(58) Field of Classification Search
USPC ........... 60/275, 276, 284, 285, 286, 300, 303; 73/114.71, 114.72, 114.73, 114.75
See application file for complete search history.

(56) References Cited

U.S. PATENT DOCUMENTS

| | | | |
|---|---|---|---|
| 7,490,596 B2* | 2/2009 | Yasui et al. ................... | 123/697 |
| 7,805,928 B2* | 10/2010 | Shouda et al. .................. | 60/285 |

(Continued)

FOREIGN PATENT DOCUMENTS

| | | |
|---|---|---|
| JP | 0988688 | 3/1997 |
| JP | 2003172177 | 6/2003 |

(Continued)

OTHER PUBLICATIONS

International Search Report for Application No. PCT/JP2012/058317 dated Apr. 24, 2012 (English Translation, 2 pages).

*Primary Examiner* — Binh Q Tran
(74) *Attorney, Agent, or Firm* — Michael Best & Friedrich LLP

(57) ABSTRACT

A heater control device of an oxygen concentration sensor is provided in which even in a case where an internal combustion engine is automatically stopped by idle stop control after cold start-up, it is possible to start energization of a heater at an appropriate time.
The heater control device includes a model temperature calculation section that calculates model temperature around the oxygen concentration sensor, a heat amount integration section that calculates an integrated heat amount by integrating the amount of heat passing through an installation position of the oxygen concentration sensor, an energization instruction section that starts the energization of the heater when the integrated heat amount has reached a predetermined energization start threshold value, a reset section that resets the integrated heat amount and the energization start threshold value at the time of stop or start-up of the internal combustion engine and, on the other hand, does not reset the integrated heat amount and the energization start threshold value at the time of automatic stop and restart of the internal combustion engine by the idle stop control, and a correction section that corrects the integrated heat amount or the energization start threshold value in consideration of the influence of heat radiation during the automatic stop of the internal combustion engine by the idle stop control.

14 Claims, 11 Drawing Sheets

(56) References Cited

U.S. PATENT DOCUMENTS

| | | | |
|---|---|---|---|
| 7,841,769 B2 * | 11/2010 | Ma et al. | 374/147 |
| 8,014,930 B2 * | 9/2011 | Anilovich et al. | 701/102 |
| 8,362,405 B2 * | 1/2013 | Hasegawa | 219/497 |

FOREIGN PATENT DOCUMENTS

| | | |
|---|---|---|
| JP | 2007138832 | 6/2007 |
| JP | 2007239480 | 9/2007 |
| JP | 2010185386 | 8/2010 |

* cited by examiner

33: MODEL TEMPERATURE CALCULATION SECTION
35: HEAT AMOUNT INTEGRATION SECTION
37: ENERGIZATION INSTRUCTION SECTION
43: HEATER DRIVING CIRCUIT
39: RESET SECTION
41: CORRECTION SECTION
31: ISS OPERATION DETECTING SECTION

S21: INITIAL TEMPERATURE SETTING

S22: MODEL TEMPERATURE CALCULATION

S23: MODEL TEMPERATURE ≥ INTEGRATION START THRESHOLD VALUE?

S31: EXHAUST GAS FLOW RATE, FUEL INJECTION AMOUNT, EXHAUST GAS TEMPERATURE, AND ENGINE SPEED ARE READ IN

S32: OXYGEN CONCENTRATION SENSOR INSTALLATION POSITION PASSING HEAT AMOUNT CALCULATION

S33: INTEGRATION

Fig. 9

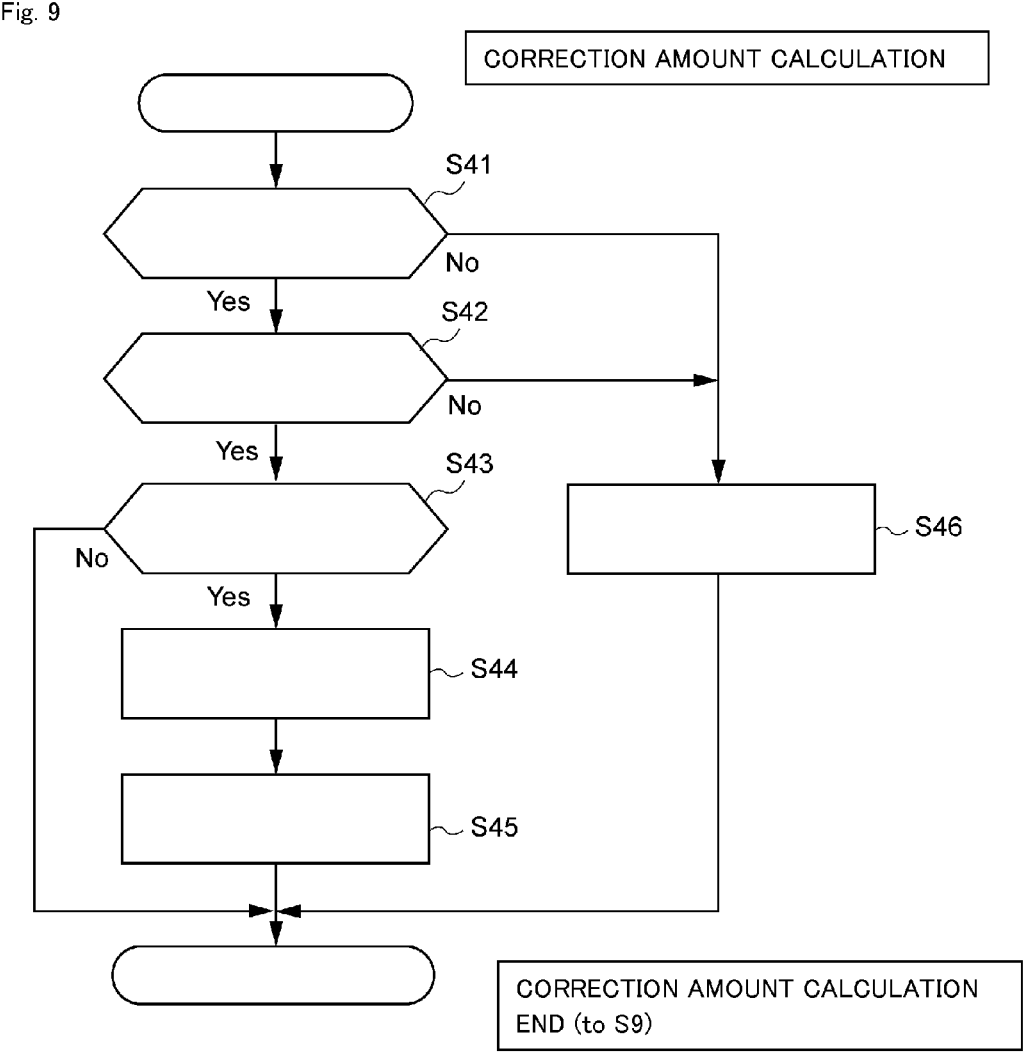

S41: MODEL TEMPERATURE ≥ INTEGRATION START THRESHOLD VALUE?

S42: ISS TIME < CORRECTION RELEASE THRESHOLD VALUE?

S43: MODEL TEMPERATURE < REQUIRED CORRECTION THRESHOLD VALUE?

S44: CALCULATION OF HEAT AMOUNT CORRECTION AMOUNT IN CALCULATION PERIOD IN THIS TIME

S45: HEAT AMOUNT CORRECTION AMOUNT INTEGRATION

S46: HEAT AMOUNT CORRECTION AMOUNT AND CORRECTION AMOUNT WITH INTEGRATED HEAT AMOUNT REFLECTED THEREIN ARE RESET

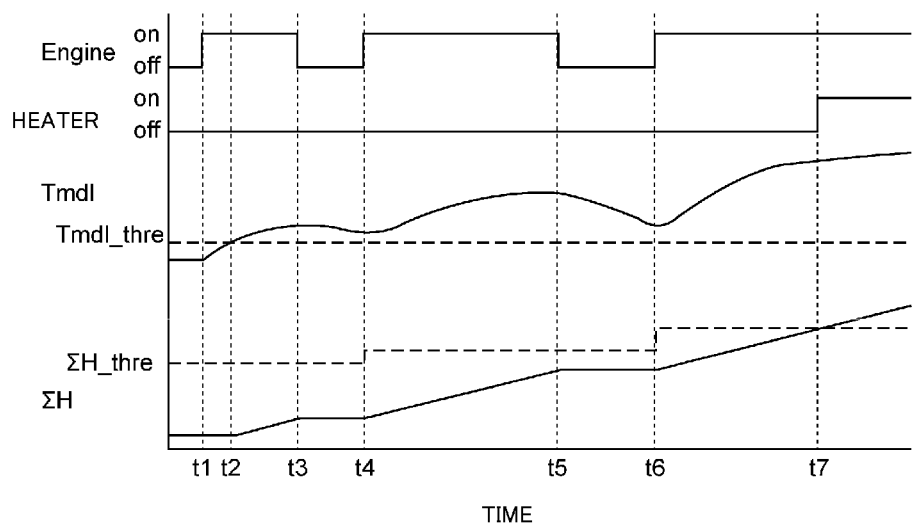

HEATER RELEASE CONTINUATION DETERMINATION

HEATER RELEASE CONTINUATION DETERMINATION END (to S53)

S61: MODEL TEMPERATURE ≥ INTEGRATION START THRESHOLD VALUE?
S62: ISS TIME < CORRECTION RELEASE THRESHOLD VALUE?
S63: HEATER RELEASE ON CONTINUATION
S64: HEATER RELEASE OFF AND HEAT AMOUNT CORRECTION AMOUNT RESET

HEATER CONTROL DEVICE OF OXYGEN CONCENTRATION SENSOR

BACKGROUND OF THE INVENTION

The present invention relates to a heater control device of an oxygen concentration sensor, which performs heater control of the oxygen concentration sensor provided in an exhaust passage of an internal combustion engine and having a heater for heating a sensor element. In particular, the present invention relates to a heater control device of an oxygen concentration sensor provided in an exhaust passage of an internal combustion engine capable of executing idle stop control.

Traditionally, an oxygen concentration sensor for detecting oxygen concentration or an excess air ratio to theoretical air fuel ratio (a lambda value) has been provided in an exhaust passage of an internal combustion engine which is typified by a diesel engine. Information that is detected by the oxygen concentration sensor is used for, for example, correction of variation in a fuel injection amount, correction of variation in an EGR amount (an exhaust gas circulation amount), abnormality diagnosis of an exhaust gas purifier, or the like.

As the oxygen concentration sensor, an oxygen concentration sensor is used which has a sensor element made of a solid electrolyte such as zirconia and is also provided with a heater for maintaining the sensor element at a predetermined activation temperature. Such an oxygen concentration sensor is made so as to be able to output a sensor signal according to oxygen concentration in exhaust gas when the sensor element has reached a temperature greater than or equal to the activation temperature by heating the sensor element with the heater.

Here, at the time of cold start-up of the internal combustion engine, since the inside of an exhaust pipe is in a low-temperature state, water vapor contained in the exhaust gas condenses, thereby becoming water droplets. The sensor element is heated to about 800 degrees by the heater, but if condensed water touches the sensor element, the sensor element will cool suddenly, and thus there is a concern that cracks in the element may occur due to thermal shock. For this reason, a configuration is made such that at the time of cold start-up of the internal combustion engine, control is performed so as to operate the heater after it is determined that all the condensed water in the exhaust pipe has evaporated.

As a method of determining that the condensed water in the exhaust pipe has evaporated in heater control, there is a method focused on a heat balance in the vicinity of a sensor installation site. For example, a heater control device of a gas sensor is disclosed which is made such that an ECU calculates heat amount data corresponding to a heat balance in the vicinity of a sensor installation site of an exhaust pipe on the basis of the operating states of an internal combustion engine and a vehicle after start-up of the internal combustion engine, performs determination of dryness in the exhaust pipe on the basis of the heat amount data, and controls an energization state of a heater on the basis of the result of the determination of dryness (refer to JP-A-2007-138832, for example).

SUMMARY OF INVENTION

Incidentally, in recent years, for the purpose of reducing noise or exhaust emission during a period of idling in an internal combustion engine mounted on a vehicle, a device configured so as to be able to execute control to automatically stop the internal combustion engine during a temporary stop of the vehicle (such control will be hereinafter referred to as "idle stop control") has begun to be put to practical use.

The heater control device of a gas sensor as described in JP-A-2007-138832 described above is made such that an integrated value of the amount of heat is first reset every time the internal combustion engine is started and such that integration of the amount of heat is then started again. Therefore, in a case where the idle stop control is repeated after the cold start-up of the internal combustion engine, the integrated value of the amount of heat is reset each time, and temperature in the vicinity of a sensor installation section remains to be recognized as low, and thus the determination of dryness in the exhaust pipe is delayed, and as a result, there is a concern that energization of the heater may be delayed. In an extreme case, a state is created where the energization of the heater is not started.

The inventors of the present invention have, in view of such a problem, found that such a problem can be solved by a configuration made so as to correct an integrated value of the amount of heat or an energization start threshold value in consideration of the influence of heat radiation without resetting the integrated value of the amount of heat which has been calculated or the energization start threshold value even at the time of automatic stop of the internal combustion engine by the idle stop control, and have completed the present invention. That is, the present invention has an object to provide a heater control device of an oxygen concentration sensor, in which it is possible to start energization of a heater at an appropriate time even in a case where an internal combustion engine is automatically stopped by the idle stop control after cold start-up.

According to the invention, there is provided a heater control device of an oxygen concentration sensor, which is provided in an exhaust pipe of an internal combustion engine capable of executing idle stop control to automatically stop the internal combustion engine during the temporary stop of a vehicle and includes a sensor element that detects oxygen concentration in exhaust gas and a heater that heats the sensor element, the heater control device controlling energization of the heater in the oxygen concentration sensor and including: a model temperature calculation section that calculates model temperature around the oxygen concentration sensor; a heat amount integration section that calculates an integrated heat amount by integrating the amount of heat passing through an installation position of the oxygen concentration sensor; an energization instruction section that starts the energization of the heater when the integrated heat amount has reached a predetermined energization start threshold value; a reset section that resets the integrated heat amount and the energization start threshold value at the time of stop or the time of start-up of the internal combustion engine and on the other hand, does not reset the integrated heat amount and the energization start threshold value at the time of automatic stop and the time of restart of the internal combustion engine by the idle stop control; and a correction section that corrects the integrated heat amount or the energization start threshold value in consideration of the influence of heat radiation during the automatic stop of the internal combustion engine by the idle stop control, and thus it is possible to solve the above-described problem.

That is, the heater control device of an oxygen concentration sensor according to the invention is configured so as to correct the integrated heat amount or the energization start threshold value in consideration of the influence of heat radiation without resetting the integrated heat amount at the installation position of the oxygen concentration sensor or the energization start threshold value at the time of the automatic stop of the internal combustion engine by the idle stop control. For this reason, even in a case where the automatic stop of the internal combustion engine by the idle stop control is repeated after start-up of the internal combustion engine, it can be made possible to start the energization of the heater at an appropriate time. Therefore, it is possible to prevent cracks in the element of the oxygen concentration sensor and it is also possible to prevent delay of the start of control using a sensor value of oxygen concentration sensor.

Further, in the heater control device of an oxygen concentration sensor according to the invention, it is preferable that the heat amount integration section start integration of the amount of heat when the model temperature has reached a predetermined integration start threshold value.

By calculating the integrated heat amount in this manner, the integrated heat amount from the time when generated condensed water begins to evaporate is calculated, and thus it can be made possible to accurately estimate the time when the condensed water disappears.

Further, in the heater control device of an oxygen concentration sensor according to the invention, it is preferable that the model temperature calculation section calculate the model temperature on the basis of a heat amount balance at the installation position of the oxygen concentration sensor and set the integration start threshold value in consideration of a decrease in temperature due to the influence of disturbance in advance.

By calculating the model temperature in this manner and also setting the integration start threshold value in this manner, it is possible to determine a calculation start time of the integrated heat amount in consideration of the influence of disturbance that is difficult to reproduce in the calculation of the model temperature.

Further, in the heater control device of an oxygen concentration sensor according to the invention, it is preferable that the correction section perform the correction in consideration of the influence of heat radiation in a period of time when assumed temperature of the installation position of the oxygen concentration sensor during the automatic stop of the internal combustion engine by the idle stop control falls below assumed temperature, in an idle state of the internal combustion engine.

By performing the correction of the integrated heat amount or the energization start threshold value in this manner, the correction is performed in a state where the influence of heat radiation exceeding the influence of disturbance considered in advance when setting the integration start threshold value is generated, and thus it can be made possible to appropriately determine a start time for energization of the heater.

Further, in the heater control device of an oxygen concentration sensor according to the invention, it is preferable that the correction section perform the correction in consideration of the influence of heat radiation in a period of time after the model temperature has become less than a predetermined required correction threshold value, after the automatic stop of the internal combustion engine by the idle stop control.

By performing the correction of the integrated heat amount or the energization start threshold value in this manner, a state where the influence of heat radiation exceeding the influence of disturbance considered in advance when setting the integration start threshold value is generated is relatively accurately grasped, and the correction is then started, and thus it can be made possible to appropriately determine the start time for energization of the heater.

Further, in the heater control device of an oxygen concentration sensor according to the invention, it is preferable that the correction section seek a difference between the assumed temperature in the idle state of the internal combustion engine and the assumed temperature during the automatic stop of the internal combustion engine by the idle stop control and subtract the amount of heat equivalent to the difference from the integrated heat amount or add the amount of heat equivalent to the difference to the energization start threshold value.

By performing the correction of the integrated heat amount or the energization start threshold value in this manner, the correction is performed in consideration of the influence of heat radiation, except for the influence of disturbance considered in advance when setting the integration start threshold value, and thus it can be made possible to more appropriately determine the start time for energization of the heater.

Further, in the heater control device of an oxygen concentration sensor according to the invention, it is preferable that the correction section integrate the amount of heat equivalent to the difference during the automatic stop of the internal combustion engine by the idle stop control and subtract an integrated value of the amount of heat from the integrated heat amount or add the integrated value of the amount of heat to the energization start threshold value at the time of restart of the internal combustion engine.

By calculating and reflecting a correction amount in this manner, it is possible to enable a reduction in a calculation load of the control device at the time of the automatic stop of the internal combustion engine.

Further, in the heater control device of an oxygen concentration sensor according to the invention, it is preferable that during the automatic stop of the internal combustion engine by the idle stop control, when a duration of the automatic stop has become greater than or equal to a predetermined correction release threshold value or when the model temperature has become less than the integration start threshold value, the correction section cease calculation of a correction amount and reset a correction amount already reflected.

In this manner, when an automatic stop time of the internal combustion engine has become greater than or equal to the correction release threshold value or when the model temperature has become less than the integration start threshold value, the calculation of the correction amount is ceased along with the correction amount already reflected being reset, whereby, when a state is created where the ambient temperature of the installation position of the oxygen concentration sensor is lowered, the integration of the amount of heat is started again after the model temperature has become greater than or equal to the integration start threshold value after the time of the next restart, and comparison with the energization start threshold value is then performed, and therefore, it is possible to enable a reduction in load of the control device while enabling the energization of the heater at an appropriate time.

Further, in the heater control device of an oxygen concentration sensor according to the invention, it is preferable that the correction section stop subsequent correction when the integrated heat amount after the correction has fallen below a predetermined lower limit or when the energization start threshold value after the correction has reached a predetermined upper limit.

In this manner, by providing the lower limit in the integrated heat amount or providing the upper limit in the energization start threshold value, a determination of an energization start time which deviates from an actual condensed water generation status is prevented, and thus it is possible to enable prevention of delay at the time of the start of energization of the heater.

In addition, in this specification, unless expressly described otherwise, in a case of being stated as "automatic stop of the internal combustion engine" or "restart of the internal combustion engine", it means stop or start-up of the internal combustion engine by the idle stop control, and in a case of being simply stated as "stop of the internal combustion engine" or "start-up of the internal combustion engine", it means stop or start-up of the internal combustion engine which does not depend on the idle stop control.

BRIEF DESCRIPTION OF DRAWINGS

FIG. 9 is a flowchart shown for describing a routine of a method of a calculating a correction amount.

FIG. 10 is a time chart shown for describing the heater control method.

DETAILED DESCRIPTION

Figure 1:
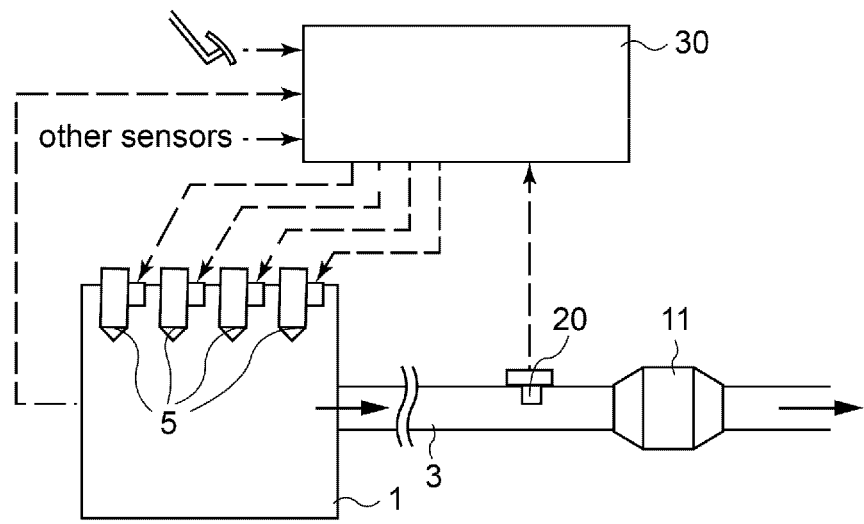
FIG. 1 is a diagram shown for describing the configuration of an exhaust system of an internal combustion engine provided with a heater control device of an oxygen concentration sensor.

Hereinafter, embodiments related to a heater control device of an oxygen concentration sensor according to the invention will be specifically described based on the drawings.

In addition, an element denoted by the same reference numeral in the respective drawings shows the same constituent element unless expressly described otherwise, and description is omitted appropriately.

Figure 2:
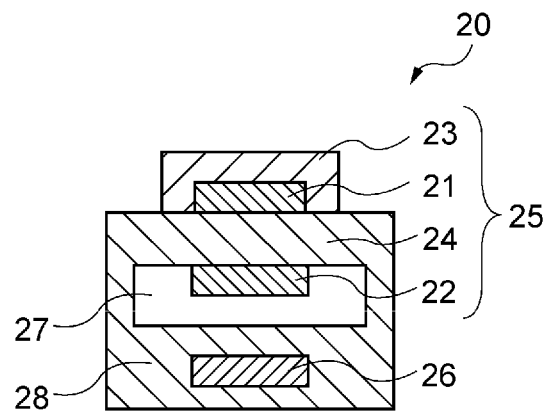
FIG. 2 is a diagram shown for describing the configuration of the oxygen concentration sensor.
Figure 3:
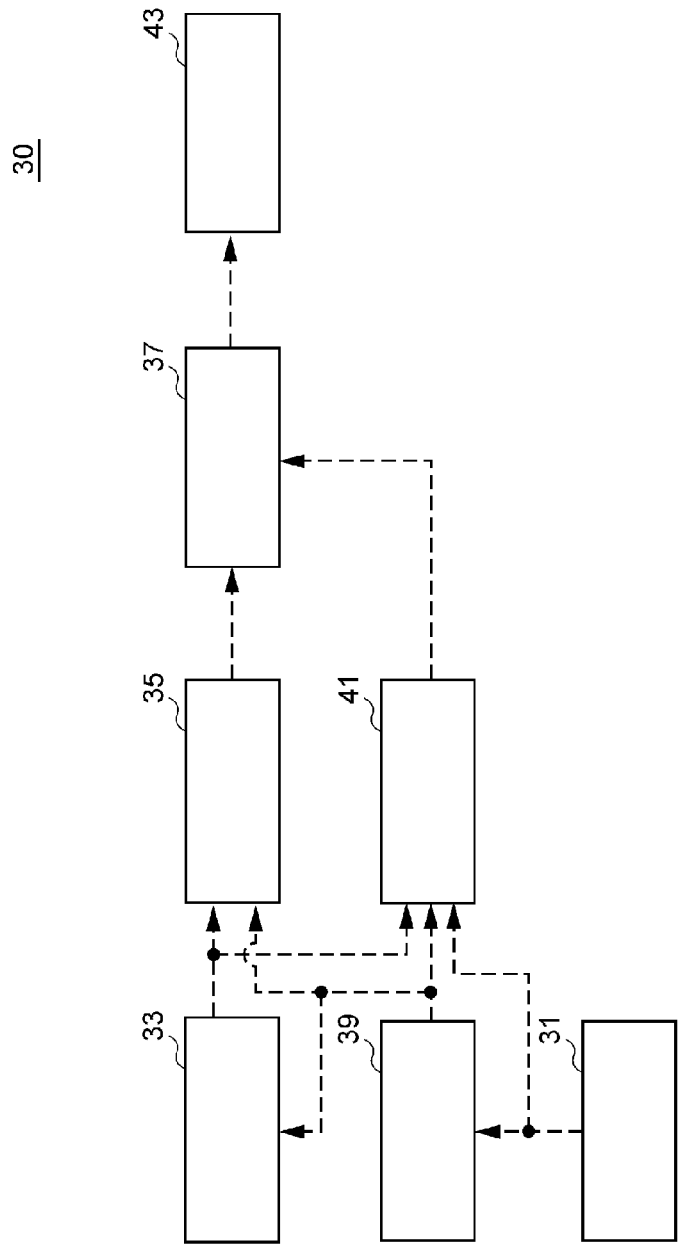
FIG. 3 is a diagram shown for describing the configuration of an electronic control device as the heater control device of the oxygen concentration sensor.
Figure 4:
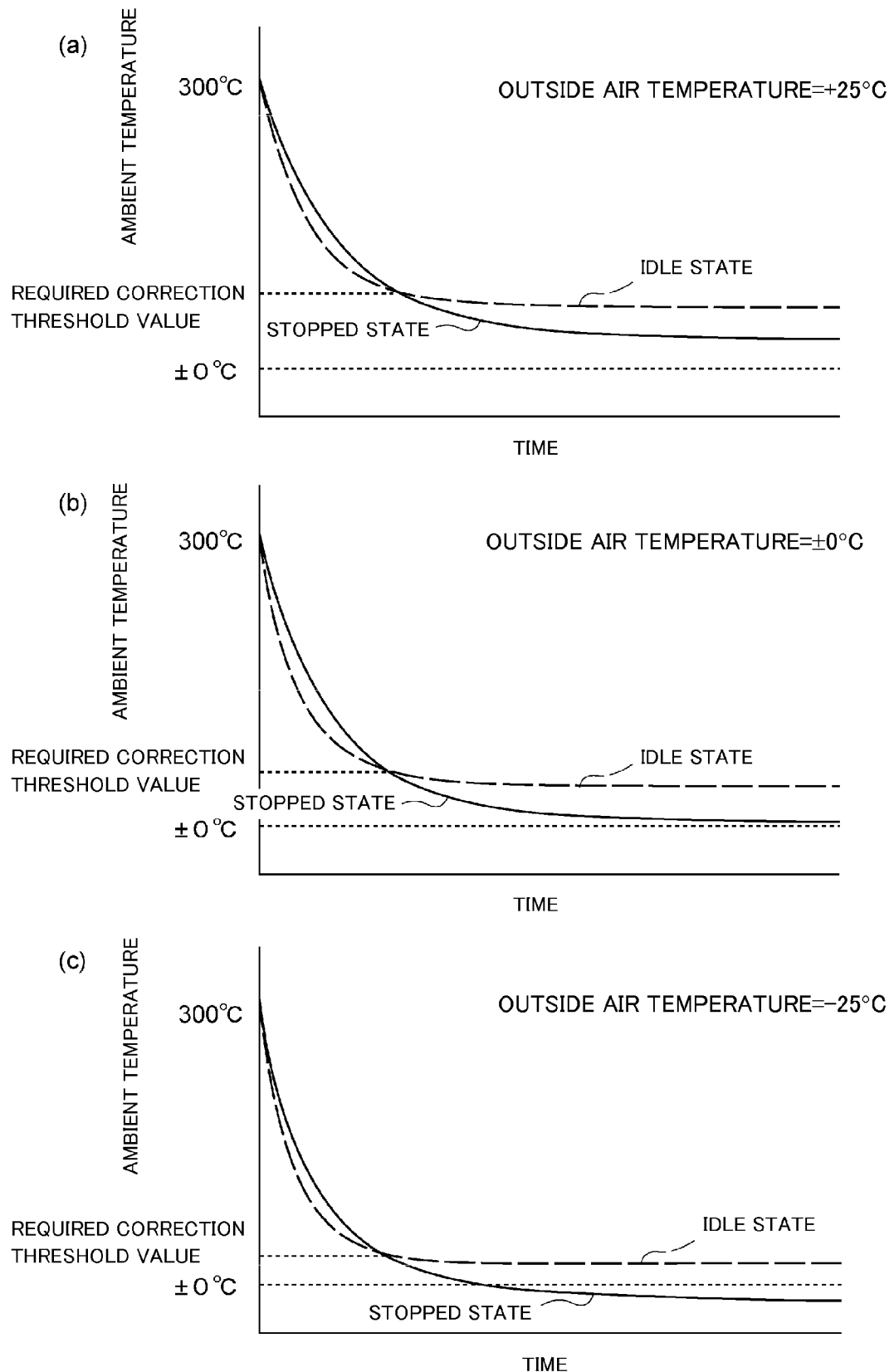
FIG. 4 is a diagram showing a change in ambient temperature of an installation position of the oxygen concentration sensor.
Figure 5:
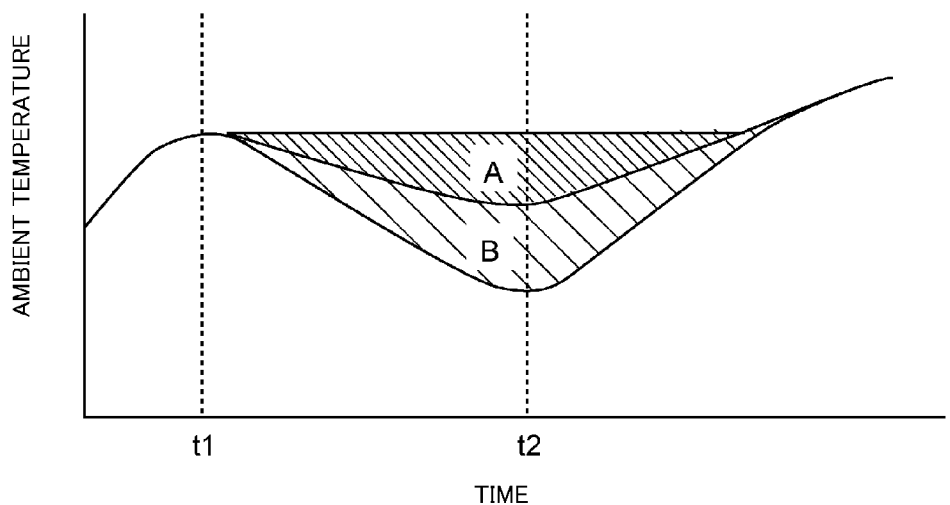
FIG. 5 is a diagram schematically showing a change in ambient temperature of the installation position of the oxygen concentration sensor.
Figure 6:
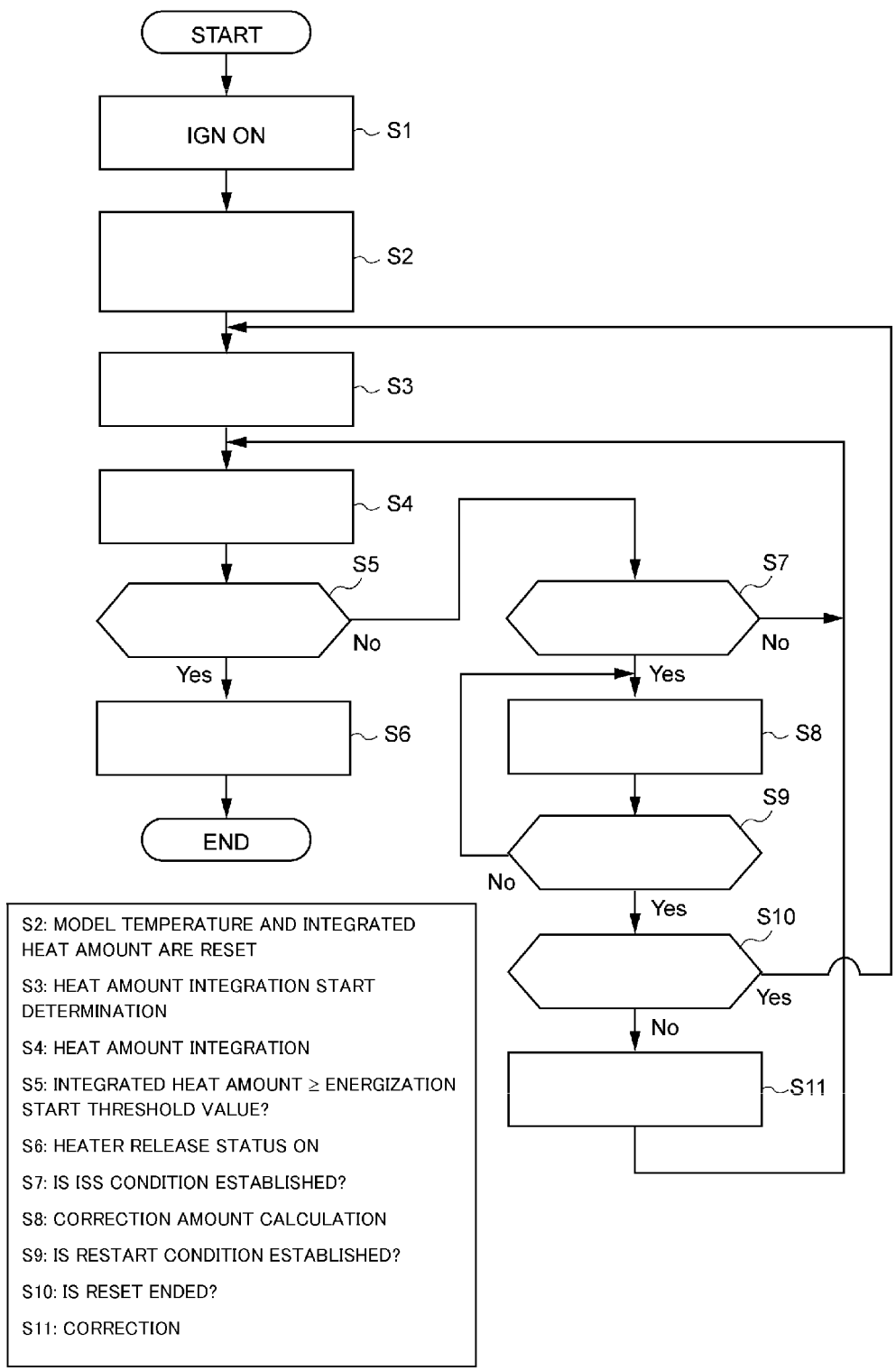
FIG. 6 is a flowchart shown for describing a main routine of a heater control method which is executed by a heater control device of an oxygen concentration sensor according to a first embodiment.
Figure 7:
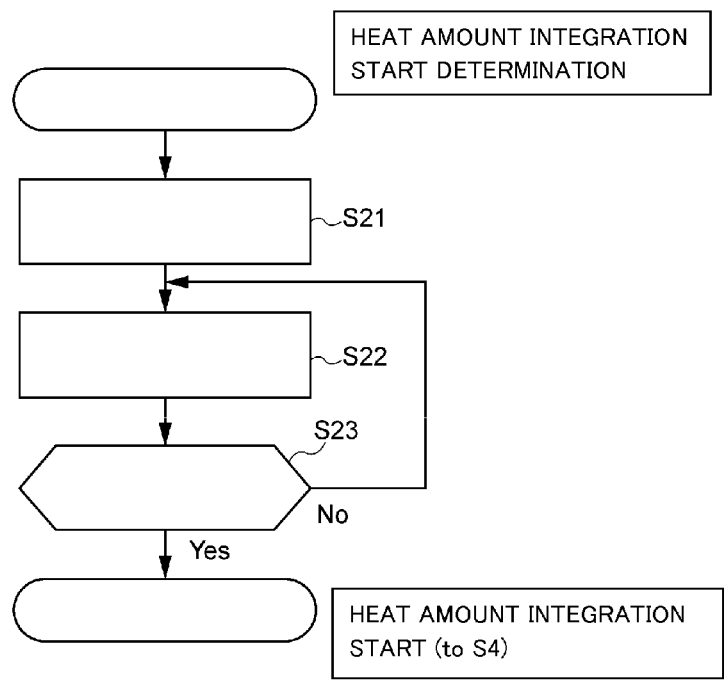
FIG. 7 is a flowchart shown for describing a routine of a method of determining a start time of heat amount integration.
Figure 8:
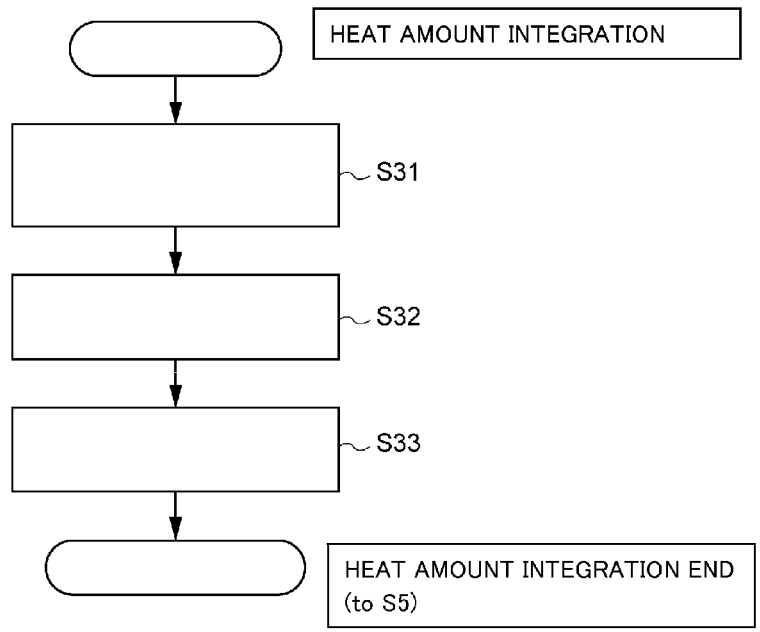
FIG. 8 is a flowchart shown for describing a routine of a method of calculating the integrated heat amount.

FIG. 1 is a diagram shown for describing the configuration of an exhaust system of an internal combustion engine provided with a heater control device of an oxygen concentration sensor. FIG. 2 is a diagram shown for describing the configuration of the oxygen concentration sensor. FIG. 3 is a diagram shown for describing the configuration of an electronic control device as the heater control device of the oxygen concentration sensor. FIG. 4 is a diagram showing a change in ambient temperature of an installation position of the oxygen concentration sensor. FIG. 5 is a diagram schematically showing a change in ambient temperature of the installation position of the oxygen concentration sensor. FIG. 6 is a flowchart shown for describing a main routine of a heater control method which is executed by a heater control device of an oxygen concentration sensor according to a first embodiment. FIG. 7 is a flowchart shown for describing a routine of a method of determining a start time of heat amount integration. FIG. 8 is a flowchart shown for describing a routine of a method of calculating the integrated heat amount. FIG. 9 is a flowchart shown for describing a routine of a method of calculating a correction amount. FIG. 10 is a time chart shown for describing the heater control method.

1. Configuration of Exhaust System of Internal Combustion Engine

In FIG. 1, an internal combustion engine 1 is typically a diesel engine and is provided with a plurality of fuel injection valves 5, and an exhaust pipe 3 which makes exhaust gas flow is connected thereto. Energization of the fuel injection valve 5 is controlled by an electronic control device 30, and the electronic control device 30 calculates a fuel injection amount on the basis of an engine speed, an accelerator operation amount, or other information and seeks an energization period and an energization time of the fuel injection valve 5 on the basis of the calculated fuel injection amount so as to execute energization control of the fuel injection valve 5.

The exhaust pipe 3 connected to the internal combustion engine 1 is provided with an exhaust gas purification member 11. The exhaust gas purification member 11 is a catalyst or a filter which is used for purifying the exhaust gas that is discharged from the internal combustion engine 1, and a single or a plurality of catalysts or filters is provided in the exhaust pipe 3 as the exhaust gas purification member 11. As the exhaust gas purification member 11, an oxidation catalyst, a particulate filter, or a NOx catalyst is typically illustrated. However, there is no particular limitation.

Further, an oxygen concentration sensor 20 is provided on the upstream side of the exhaust gas purification member 11. A sensor signal of the oxygen concentration sensor 20 is input to the electronic control device 30. The relationship between an installation position of the oxygen concentration sensor 20 and an installation position of the exhaust gas purification member 11 is not particularly limited, and the oxygen concentration sensor 20 may be provided on the downstream side of the exhaust gas purification member 11 and the oxygen concentration sensor 20 may also be provided between a plurality of catalysts or filters.

2. Configuration of Oxygen Concentration Sensor

FIG. 2 schematically shows the configuration of the oxygen concentration sensor 20. The oxygen concentration sensor 20 has a sensor element 25 which includes a first electrode 21, a second electrode 22, a protective layer 23, and a solid electrolyte layer 24. The solid electrolyte layer 24 is disposed between the first electrode 21 and the second electrode 22. The first electrode 21 is covered by the protective layer 23 and the protective layer 23 is exposed to the exhaust gas in the exhaust pipe 3. The second electrode 22 is disposed in a reference gas chamber 27.

Further, a heater 26 is provided in a solid electrolyte body 28 which is located on the side opposite to the solid electrolyte layer 24 with the reference gas chamber 27 interposed therebetween. The heater 26 is configured as a heat generation resistor which generates heat due to energization, and energization control thereof is performed by the electronic control device 30. Since the sensor element 25 is made so as to be able to detect oxygen concentration by being activated in a state of being greater than or equal to a predetermined temperature, at the time of start-up of the internal combustion engine 1, the heater 26 is energized so as to heat the sensor element 25.

3. Electronic Control Device (Heater Control Device)

(1) Basic Configuration

FIG. 3 shows sections which are related to heater control of the oxygen concentration sensor 20 in the configuration of the electronic control device 30, in functional blocks. The electronic control device 30 has a function as the heater control device of an oxygen concentration sensor.

The electronic control device 30 is a device configured with a focus on a known microcomputer and is provided with an ISS operation detecting section 31, a model temperature calculation section 33, a heat amount integration section 35, an energization instruction section 37, a reset section 39, and a correction section 41. Specifically, each means is made so as to be realized by the execution of a program by a microcomputer.

Further, the electronic control device 30 is provided with a storage section (not shown) configured of a storage element such as a RAM or a ROM, and a heater driving circuit 43 for performing the energization of the heater 26 of the oxygen concentration sensor 20. In the storage section, a control program and various calculation maps are stored in advance and the calculation result or the like by each section described above is written.

The ISS operation detecting section 31 is configured so as to detect an automatically stopped state of the internal combustion engine 1 by idle stop control. Specifically, the ISS operation detecting section 31 is configured so as to detect a period of time from when an idle stop condition is established until a restart condition is established, as the automatically stopped state of the internal combustion engine 1.

The model temperature calculation section 33 is configured so as to calculate model temperature Tmdl around the installation position of the oxygen concentration sensor 20. Specifically, the model temperature calculation section 33 is configured so as to calculate the model temperature Tmdl on the basis of initial temperature T0 at the time of the start-up of the internal combustion engine 1 by estimating increase and decrease in ambient temperature on the basis of a heat amount balance around the installation position of the oxygen concentration sensor 20. The ambient temperature can be set to be, for example, the wall temperature of the exhaust pipe 3 of the installation position of the oxygen concentration sensor 20. The initial temperature T0 can be set to be a temperature which is detected by a temperature sensor provided in an intake system or an exhaust system of the internal combustion engine 1. However, in addition to this, it is possible to adopt various methods such as setting the initial temperature T0 by using information correlated with the ambient temperature of the installation position of the oxygen concentration sensor 20.

The heat amount integration section 35 is configured so as to integrate the amount of heat H passing through the installation position of the oxygen concentration sensor 20 and calculate an integrated heat amount $\Sigma H$, in a state where the model temperature Tmdl is greater than or equal to an integration start threshold value Tmdl_thre, during an automatic stop of the internal combustion engine 1 by the idle stop control. Specifically, the heat amount integration section 35 is configured so as to determine whether or not the model temperature Tmdl that is calculated in the model temperature calculation section 33 is greater than or equal to the integration start threshold value Tmdl_thre and start the integration of the amount of heat H when the model temperature Tmdl has become greater than or equal to the integration start threshold value Tmdl_thre. The integration start threshold value Tmdl_thre is for determining whether or not the ambient temperature of the installation position of the oxygen concentration sensor 20 reaches temperature at which condensed water can evaporate and can be set to an optimum value in advance according to an aspect or the like of the internal combustion engine 1 or the exhaust system thereof.

However, in the electronic control device 30 according to the first embodiment, the relationship between the initial temperature T0 and a reference temperature (dew-point temperature) at which the generated condensed water can evaporate is sought in advance by experiment or the like, and the integration start threshold value Tmdl_thre is set by adding an amount of decrease in temperature by the influence of disturbance that cannot be reproduced in the calculation of the model temperature Tmdl. That is, in the electronic control device 30 according to the first embodiment, the influence on the ambient temperature of the installation position of the oxygen concentration sensor 20 due to disturbance such as wind is not incorporated into the calculation of the model temperature Tmdl but is incorporated into the integration start threshold value Tmdl_thre in advance. The integration start threshold value Tmdl_thre may be a fixed value and may also be a value which varies depending on operating conditions of the internal combustion engine 1, environmental conditions around the exhaust system, or the like.

The energization instruction section 37 is configured so as to output an instruction signal to the heater driving circuit 43 so as to perform the energization of the heater 26 provided in the oxygen concentration sensor 20, by turning on a heater release status when the integrated heat amount $\Sigma H$ which is calculated in the heat amount integration section 35 has reached a predetermined energization start threshold value $\Sigma H\_thre$. In the electronic control device 30 according to the first embodiment, the energization start threshold value $\Sigma H\_thre$ can be set to an optimum value in advance by experiment or the like, as a value equivalent to the total amount of heat which is required from when the condensed water begins to evaporate until evaporation of all the condensed water is completed, in a case where the internal combustion engine 1 is not automatically stopped by the idle stop control.

The reset section 39 is configured so as to first reset the model temperature Tmdl, the integrated heat amount $\Sigma H$, and the energization start threshold value $\Sigma H\_thre$ stored in the storage section, when an ignition switch has been turned on. However, setting is made so as not to reset the model temperature Tmdl, the integrated heat amount $\Sigma H$, the energization start threshold value $\Sigma H\_thre$ at the time of restart after the automatic stop of the internal combustion engine 1 by the idle stop control.

The correction section 41 is configured so as to correct the energization start threshold value $\Sigma H\_thre$ in consideration of the influence of heat radiation during the automatic stop of the internal combustion engine 1 by the idle stop control.

That is, the electronic control device 30 according to the first embodiment is configured so as to be able to start the energization of the heater 26 of the oxygen concentration sensor 20 at an appropriate time by correcting the energization start threshold value $\Sigma H\_thre$ in consideration of the influence of heat radiation during the automatic stop, without resetting the model temperature Tmdl, the integrated heat amount $\Sigma H$, and the energization start threshold value $\Sigma H\_thre$ in a case where the internal combustion engine 1 has been automatically stopped and restarted by the idle stop control.

An outline of the correction which is executed by the correction section 41 of the electronic control device 30 according to the first embodiment will be described in detail with reference to FIGS. 4 and 5.

In the storage section of the electronic control device 30 according to the first embodiment, information obtained by seeking a change in ambient temperature in an idle state and a change in ambient temperature in a stopped state of the internal combustion engine 1 by experiment or the like in advance according to outside air temperature and the ambient temperature of the installation position of the oxygen concentration sensor 20 when the internal combustion engine 1 has entered the idle state or the stopped state is stored. FIGS. 4(a) to 4(c) respectively show examples of a change in the ambient temperature of the installation position of the oxygen concentration sensor 20 when the outside air temperature is 25° C., 0° C., and −25° C.

As can be understood from FIGS. 4(a) to 4(c), in a predetermined period of time after the internal combustion engine 1 has entered the idle state or the stopped state, the amount of decrease in temperature in the idle state exceeds the amount of decrease in temperature in the stopped state. This is because the ambient temperature is forcibly cooled by a low-temperature exhaust gas. On the other hand, after a predetermined period of time has elapsed since the internal combustion engine 1 has entered the idle state or the stopped state, the amount of decrease in temperature in the stopped state exceeds the amount of decrease in temperature in the idle state. This is because in a state where the ambient temperature has been lowered to some extent, the influence of heat radiation due to the outside air temperature lower than exhaust gas temperature in the idle state becomes large.

For this reason, the correction section 41 of the electronic control device 30 according to the first embodiment is configured so as to set temperature when assumed temperature in the idle state coincides with assumed temperature in the stopped state to be a required correction threshold value and correct the energization start threshold value $\Sigma H\_thre$ in consideration of the influence of heat radiation in a period of time after the model temperature Tmdl has fallen below the required correction threshold value, after the internal combustion engine 1 has been automatically stopped by the idle stop control.

Specifically, after the model temperature Tmdl has become less than the required correction threshold value, the correction section 41 seeks a difference between the assumed temperature in the idle state and the assumed temperature in the stopped state according to an elapsed time since automatic stop, with reference to information of the amount of decrease in temperature illustrated in FIGS. 4(a) to 4(c) and converts the difference in temperature to the amount of heat. An elapsed time since the model temperature Tmdl has become less than the required correction threshold value, rather than the elapsed time since automatic stop, may be adopted. Then, the correction section 41 continues the integration of the amount of heat until the internal combustion engine 1 is restarted and makes the obtained value a heat amount correction amount for correcting the energization start threshold value $\Sigma H\_thre$.

FIG. 5 schematically shows a change in the ambient temperature of the installation position of the oxygen concentration sensor 20 after the internal combustion engine 1 has entered the idle state or the stopped state. In FIG. 5, the internal combustion engine 1 enters the idle state or the stopped state at a point in time of t1, and each state is released at the point in time of t2.

The ambient temperature is temporarily lowered in the idle state. However, in the electronic control device 30 according to the first embodiment, with respect to the amount of heat which is lost by the amount of decrease in temperature (≈ shaded area A), the amount of heat is considered as the influence of disturbance when setting the integration start threshold value Tmdl_thre. That is, unless the automatically stopped state of the internal combustion engine 1 by the idle stop control is created, it is not necessary to correct the energization start threshold value $\Sigma H\_thre$.

On the other hand, in the stopped state of the internal combustion engine 1, the amount of decrease in ambient temperature exceeds the amount of decrease in temperature in the idle state. The correction section 41 of the electronic control device 30 in the first embodiment corrects the energization start threshold value $\Sigma H\_thre$ in consideration of the amount of heat which is further lost by the amount of decrease in temperature corresponding to an amount which is not considered as the influence of disturbance (≈ shaded area B).

(2) Control Method

Next, the heater control method which is executed by the electronic control device 30 according to the first embodiment will be specifically described.

(2-1) Flowcharts

FIGS. 6 to 9 show flowcharts of a heater control that is executed by the electronic control device 30 according to the first embodiment. In addition, a routine of the heater control is made so as to be always executed at the time of the start-up of the internal combustion engine 1.

First, if an ignition switch is turned on in step S1, in step S2, the model temperature Tmdl, the integrated heat amount $\Sigma H$, and the energization start threshold value $\Sigma H\_thre$ stored in the storage section are reset. Subsequently, in step S3, a determination of whether or not the heat amount integration is started is performed.

FIG. 7 is a flowchart showing an example of a method of determining whether or not the heat amount integration is started. In this example, after the initial temperature T0 is first set on the basis of information of a sensor such as an intake air temperature sensor or an exhaust gas temperature sensor in step S21, in step S22, the model temperature Tmdl around the installation position of the oxygen concentration sensor 20 is calculated. The model temperature Tmdl can be calculated, for example, by converting a heat amount balance between a received heat amount and a heat radiation amount at the installation position of the oxygen concentration sensor 20 to the amount of change in temperature and adding it to the initial temperature T0.

Specifically, the amount of change in temperature per unit period is obtained by calculating the received heat amount from information such as exhaust gas temperature, an engine speed, or a fuel injection amount by using map information or the like stored in the storage section or the like in advance along with calculating the heat radiation amount from information such as outside air temperature or a vehicle speed and by converting an effective heat amount obtained by subtracting the heat radiation amount from the received heat amount to the amount of change in temperature. Thereafter, the model temperature Tmdl is calculated by adding the amount of change in temperature to the initial temperature T0. However, the method of calculating the model temperature Tmdl is not limited to this example.

If the model temperature Tmdl is calculated in step S22, subsequently, in step S23, whether or not the model temperature Tmdl has reached the integration start threshold value Tmdl_thre is determined. In a case where the model temperature Tmdl is less than the integration start threshold value Tmdl_thre (a case of No) in step S23, the routine returns back to step S22 and the calculation and the determination of the model temperature Tmdl are repeated until the model temperature Tmdl becomes greater than or equal to the integration start threshold value Tmdl_thre. On the other hand, in a case where the model temperature Tmdl is greater than or equal to the integration start threshold value Tmdl_thre (a case of Yes) in step S23, the determination of whether or not the heat amount integration is started is ended, and then the routing proceeds to step S4, and the integration of the amount of heat passing through the installation position of the oxygen concentration sensor 20 is started.

FIG. 8 is a flowchart showing an example of a method of calculating the integrated heat amount $\Sigma H$. In this example, first, in step S31, information such as an exhaust gas flow rate, a fuel injection amount, an exhaust gas temperature, and an engine speed is read. The information may be information detected by using a sensor and may also be information estimated by calculation.

Subsequently, in step S32, the amount of heat H which has passed through the installation position of the oxygen concentration sensor 20 in a calculation period in this time is calculated on the basis of the information read in step S31. Specifically, in the electronic control device 30 according to the first embodiment, the passing heat amount H per unit period is calculated by subtracting the dew-point temperature (=the integration start threshold value Tmdl_thre) from the exhaust gas temperature of an inlet portion of the exhaust pipe where the oxygen concentration sensor 20 is installed and multiplying this by the specific heat of the exhaust gas and an exhaust gas mass flow rate. Then, in step S33, the integrated heat amount $\Sigma H$ is updated by adding the amount of heat H per unit time obtained in step S32 to the integrated heat amount $\Sigma H$ already stored, and thereafter, the routine proceeds to step S5. The specific heat of the exhaust gas can be set in advance.

Returning back to FIG. 6, after the integrated heat amount $\Sigma H$ is obtained in step S4, in step S5, whether or not the integrated heat amount $\Sigma H$ is greater than or equal to the energization start threshold value $\Sigma H\_thre$ is determined. In a case where the integrated heat amount $\Sigma H$ is less than the energization start threshold value $\Sigma H\_thre$ (a case of No), the routine proceeds to step S7, and whether or not the internal combustion engine 1 has entered the automatically stopped state by the idle stop control is determined. In a case where the internal combustion engine 1 does not enter the automatically stopped state by the idle stop control (a case of No), the routine returns back to step S4 and the integration of the amount of heat H and comparison of the integrated heat amount $\Sigma H$ with the energization start threshold value $\Sigma H\_thre$ are repeated.

On the other hand, in a case where the internal combustion engine 1 has entered the automatically stopped state by the idle stop control (a case of Yes) in step S7, the routine proceeds to step S8 and the calculation of the correction amount is performed.

FIG. 9 is a flowchart showing an example of a method of calculating the correction amount. In this example, first, in step S41, whether or not the model temperature Tmdl around the installation position of the oxygen concentration sensor 20 is greater than or equal to the integration start threshold value Tmdl_thre is determined. Although it does not appear on the flowchart, the model temperature Tmdl is continuously calculated according to the procedure of step S21 to step S22 of FIG. 7.

In a case where the model temperature Tmdl is less than the integration start threshold value Tmdl_thre (a case of No), since a concern that condensed water may be generated is high, the routine proceeds to step S46 and the heat amount correction amount stored in the storage section, the heat amount correction amount already reflected, and the integrated heat amount $\Sigma H$ are reset, and the routing proceeds to step S9. In this case, when the internal combustion engine 1 has been restarted, similar to the time of the stop of the internal combustion engine 1 that does not depend on the idle stop control, the heat amount integration is not started until the model temperature Tmdl becomes greater than or equal to the integration start threshold value Tmdl_thre.

On the other hand, in a case where the model temperature Tmdl is greater than or equal to the integration start threshold value Tmdl_thre (a case of Yes) in step S41, the routine proceeds to step S42 and whether or not duration of the automatic stop of the internal combustion engine 1 by the idle stop control is less than a correction release threshold value is determined. In a case where the duration is greater than or equal to the correction release threshold value (a case of No), since the ambient temperature of the installation position of the oxygen concentration sensor 20 is lowered and thus a concern that condensed water may be generated is high, the routine proceeds to step S46 and the heat amount correction amount stored in the storage section, the heat amount correction amount already reflected, and the integrated heat amount H are reset, and the routing proceeds to step S9. Also in this case, when the internal combustion engine 1 has been restarted, similar to the time of the stop of the internal combustion engine 1 that does not depend on the idle stop control, the heat amount integration is not started until the model temperature Tmdl becomes greater than or equal to the integration start threshold value Tmdl_thre.

On the other hand, in a case where the duration is less than the correction release threshold value (a case of Yes) in step S42, the routine proceeds to step S43 and whether or not the model temperature Tmdl is less than the required correction threshold value is determined. In a case where the model temperature Tmdl is not less than the required correction threshold value (a case of No), the calculation of the heat amount correction amount is not performed in the calculation period in this time, and the routine returns back to step S9.

On the other hand, in a case where the model temperature Tmdl is less than the required correction threshold value (a case of Yes), the routine proceeds to step S44 and the heat amount correction amount in the calculation period in this time is calculated. If the heat amount correction amount in the calculation period in this time is obtained, subsequently, in step S45, the heat amount correction amount is updated by adding the heat amount correction amount in the calculation period in this time to the heat amount correction amount stored in the storage section.

Describing the integration of the heat amount correction amount in step S43 to step S45 with reference to FIGS. 4 and 5, as illustrated in FIGS. 4(a) to 4(c), if a predetermined period of time elapses since the internal combustion engine 1 has entered the idle state or the stopped state, the amount of decrease in temperature in the stopped state exceeds the amount of decrease in temperature in the idle state. For this reason, in step S43, whether or not the model temperature Tmdl is less than the required correction threshold value is determined with the temperature when the assumed temperature in the idle state coincides with the assumed temperature in the stopped state set as the required correction threshold value.

Further, in step S44, a difference between the assumed temperature in the idle state and the assumed temperature in the stopped state is sought according to an elapsed time since automatic stop with reference to information of the amount of decrease in temperature illustrated in FIGS. 4(a) to 4(c), the difference in temperature is converted to the amount of heat, and the amount of heat is set to be the heat amount correction amount in the calculation period in this time. An elapsed time since the model temperature Tmdl has become less than the required correction threshold value, rather than the elapsed time since automatic stop, may be adopted.

Then, in step S45, the heat amount correction amount is integrated. An integration value of the heat amount correction amount that is obtained in step S45 is the total amount of the heat radiation amount which is not considered when setting the energization start threshold value ΣH_thre and is generated in a period of time from the time of the automatic stop of the internal combustion engine 1 by the idle stop control to the calculation period in this time. If the integration of the heat amount correction amount is ended, the routine proceeds to step S9.

Returning back to FIG. 6, if the correction amount calculation process in step S8 is ended, the routine proceeds to step S9 and whether or not the restart condition of the internal combustion engine 1 is established is determined. The calculation of the correction amount in step S8 and the determination of the establishment of the restart condition in step S9 are repeated until the restart condition is established.

In a case where the restart condition is established (a case of Yes) in step S9, the routine proceeds to step S10 and whether or not the heat amount correction amount calculated during the automatic stop in this time, the correction amount already reflected in the energization start threshold value ΣH_thre, and the integrated heat amount ΣH have been reset is determined. In a case of a reset end state (a case of Yes), the routine returns back to step S3 and the calculation is restarted from the beginning, similar to the time of the stop of the internal combustion engine 1 that does not depend on the idle stop control.

On the other hand, in a case where the heat amount correction amount or the like has not been reset (a case of No), the routine proceeds to step S11 and the energization start threshold value ΣH_thre is updated by adding the heat amount correction amount obtained in step S8 to the energization start threshold value ΣH_thre. At this time, the upper limit is set to the energization start threshold value ΣH_thre, and in a case where the energization start threshold value ΣH_thre after the updating exceeds the upper limit, it is preferable to set the upper limit to be the energization start threshold value ΣH_thre. By providing the upper limit in the energization start threshold value ΣH_thre, an energization start time is prevented from being determined to deviate from an actual condensed water generation status, and thus it is possible to prevent delay of the start of energization of the heater 26.

After the energization start threshold value ΣH_thre is obtained, the routine returns back to step S4 and the steps up to this step are repeatedly performed. Then, in a case where the integrated heat amount ΣH has reached the energization start threshold value ΣH_thre (a case of Yes) in step S5, since it is estimated that all the condensed water disappears at the installation position of the oxygen concentration sensor 20, the routine proceeds to step S6, and the heater release status is turned on, and thus the energization of the heater 26 of the oxygen concentration sensor 20 is started, and thereafter, this routine is ended.

The heater control method described up to here which is represented by a time chart is as shown in FIG. 10. FIG. 10 shows a time chart showing transitions of an operating state of the internal combustion engine 1, an energization state of the heater 26, the model temperature, and the integrated heat amount.

If the internal combustion engine 1 is started at a point in time of t1, the electronic control device 30 starts the calculation of the model temperature Tmdl from that point in time. Subsequently, if the model temperature Tmdl reaches the integration start threshold value Tmdl_thre at a point in time of t2, the electronic control device 30 starts the calculation of the integrated heat amount ΣH.

Subsequently, if the internal combustion engine 1 enters the automatically stopped state by the idle stop control at a point in time of t3, the calculation of the integrated heat amount ΣH is interrupted up to a point in time of t4 when restart is performed. Further, during this period, the model temperature Tmdl is lowered. However, the electronic control device 30 does not correct the integrated heat amount ΣH and, on the other hand, adds the heat radiation amount, which is integrated in this period, to the energization start threshold value ΣH_thre at the time of the restart.

After a point in time of t4 when the internal combustion engine 1 is restarted, the electronic control device 30 restarts the calculation of the integrated heat amount ΣH. Thereafter, also in periods of time of t5 to t6 when the internal combustion engine 1 is automatically stopped by the idle stop control, the correction of the energization start threshold value ΣH_thre is performed in the same way.

Then, if the integrated heat amount ΣH reaches the energization start threshold value ΣH_thre at a point in time of t7, the electronic control device 30 starts the energization of the heater 26.

As described above, according to the heater control device of an oxygen concentration sensor related to the first embodiment, a configuration is made so as to correct the energization start threshold value ΣH_thre in consideration of the influence of heat radiation without resetting the model temperature Tmdl at the installation position of the oxygen concentration sensor 20, the integrated heat amount ΣH, or the energization start threshold value ΣH_thre, at the time of the automatic stop of the internal combustion engine 1 by the idle stop control. For this reason, even in a case where the automatic stop and the restart of the internal combustion engine 1 by the idle stop control are repeated after the start-up of the internal combustion engine 1, it can be made possible to start the energization of the heater 26 of the oxygen concentration sensor 20 at an appropriate time. Therefore, it is possible to prevent cracks in the element of the oxygen concentration sensor 20, and it is also possible to prevent delay of the start of control using the sensor value of the oxygen concentration sensor 20.

Further, in the heater control device of an oxygen concentration sensor according to the first embodiment, the heat amount integration section 35 starts the integration of the amount of heat when the model temperature Tmdl has reached the integration start threshold value Tmdl_thre. Therefore, the integrated heat amount from the time when the generated condensed water begins to evaporate is calculated, and thus it can be made possible to accurately estimate the time when the condensed water disappears.

Further, in the heater control device of an oxygen concentration sensor according to the first embodiment, the model temperature calculation section 33 calculates the model temperature Tmdl on the basis of a heat amount balance at the installation position of the oxygen concentration sensor 20 and sets the integration start threshold value Tmdl_thre in consideration of a decrease in temperature due to the influence of beforehand disturbance. Therefore, it is possible to determine a calculation start time of the integrated heat amount in consideration of the influence of disturbance that is difficult to reproduce, in the calculation of the model temperature Tmdl.

Further, in the heater control device of an oxygen concentration sensor according to the first embodiment, the correction section 41 performs correction in consideration of the influence of heat radiation in a period of time when the assumed temperature of the installation position of the oxygen concentration sensor 20 during the automatic stop of the internal combustion engine 1 by the idle stop control falls below the assumed temperature in the idle state of the internal combustion engine 1. Therefore, correction is performed in a state where the influence of heat radiation exceeding the influence of disturbance considered in advance when setting the integration start threshold value Tmdl_thre is generated, and thus it can be made possible to appropriately determine the start time for energization of the heater 26.

Further, in the heater control device of an oxygen concentration sensor according to the first embodiment, the correction section 41 performs correction in consideration of the influence of heat radiation in a period of time after the model temperature Tmdl has become less than the required correction threshold value, after the automatic stop of the internal combustion engine 1 by the idle stop control. Therefore, a state where the influence of heat radiation exceeding the influence of disturbance considered in advance when setting the integration start threshold value Tmdl_thre is generated is grasped relatively accurately, and then the correction can be started, and thus it can be made possible to appropriately determine the start time for energization of the heater 26.

Further, in the heater control device of an oxygen concentration sensor according to the first embodiment, the correction section 41 seeks a difference between the assumed temperature in the idle state of the internal combustion engine 1 and the assumed temperature during the automatic stop of the internal combustion engine 1 by the idle stop control, converts the difference in temperature to the amount of heat, and then adds the amount of heat to the energization start threshold value $\Sigma H\_thre$. Therefore, the correction is performed in consideration of the influence of heat radiation except for the influence of disturbance considered in advance when setting the integration start threshold value Tmdl_thre, and thus it can be made possible to more appropriately determine the start time for energization of the heater 26.

Further, in the heater control device of an oxygen concentration sensor according to the first embodiment, the correction section 41 integrates the amount of heat equivalent to a difference between the assumed temperature in the idle state and the assumed temperature in the stopped state during the automatic stop of the internal combustion engine 1 by the idle stop control and adds an integrated value of the amount of heat to the energization start threshold value $\Sigma H\_thre$ as the heat amount correction amount at the time of the restart of the internal combustion engine 1. Therefore, it is possible to enable reductions in a calculation load and a load of adaptation of the electronic control device 30 at the time of the automatic stop of the internal combustion engine 1.

Further, in the heater control device of an oxygen concentration sensor according to the first embodiment, when the duration of the automatic stop of the internal combustion engine 1 by the idle stop control has become greater than or equal to a predetermined correction release threshold value and when the model temperature Tmdl has become less than the integration start threshold value Tmdl_thre, the correction section 41 ceases the calculation of the correction amount and resets the correction amount already reflected. Therefore, when the ambient temperature of the installation position of the oxygen concentration sensor 20 is lowered and thus a state where condensed water is easily generated is created, the integration of the amount of heat is started again after the model temperature Tmdl has become greater than or equal to the integration start threshold value Tmdl_thre after the time of the next restart, and comparison with the energization start threshold value $\Sigma H\_thre$ is then performed, and therefore, it is possible to enable a reduction in load of the electronic control device 30 while enabling the energization of the heater at an appropriate time.

Further, in the heater control device of an oxygen concentration sensor according to the first embodiment, since the upper limit is provided in the energization start threshold value $\Sigma H\_thre$, the energization start time is prevented from being determined to deviate from an actual condensed water generation status, and thus it is possible to enable prevention of delay at the time of the start of energization of the heater.

A heater control device of an oxygen concentration sensor according to a second embodiment of the invention is configured in the same way as the heater control device of an oxygen concentration sensor according to the first embodiment with respect to a process until the energization of the heater is started. However, the heater control device of an oxygen concentration sensor according to the second embodiment is configured so as to be able to stop the energization of the heater in consideration of the ambient temperature of the installation position of the oxygen concentration sensor during the automatic stop of the internal combustion engine by the idle stop control after the energization of the heater is started once.

Figure 11:
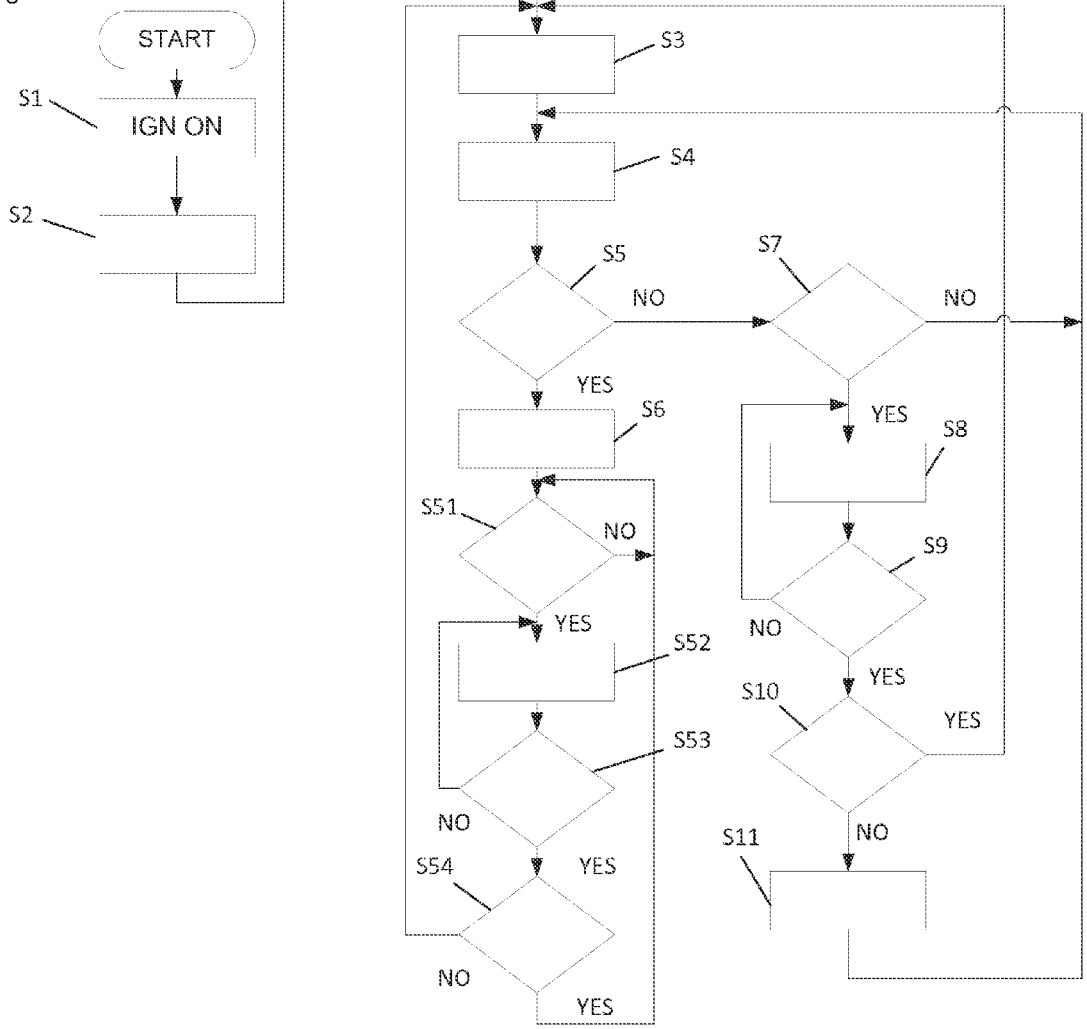
FIG. 11 is a flowchart shown for describing a main routine of a heater control method which is executed by a heater control device of an oxygen concentration sensor according to a second embodiment.
Figure 12:
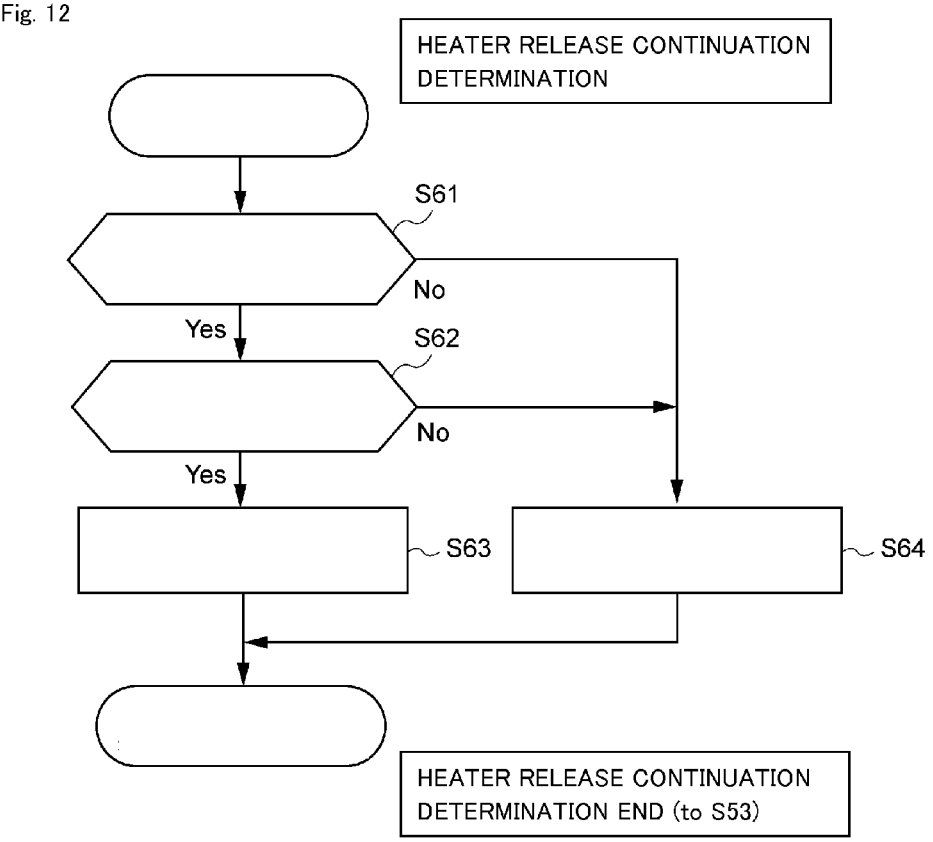
FIG. 12 is a flowchart showing a routine of a method of determining heater release continuation.

FIG. 11 is a flowchart shown for describing a main routine of a heater control method which is executed by the heater control device of an oxygen concentration sensor according to the second embodiment. FIG. 12 is a flowchart showing a routine of a method of determining heater release continuation. Hereinafter, the heater control method which is executed by the heater control device of an oxygen concentration sensor according to the second embodiment will be described along these flowcharts. With respect to the configuration of the exhaust system, since it is possible to make the configuration be equal to that in the case of the first embodiment, FIGS. 1 and 2 are referenced.

In the heater control device according to the second embodiment, as shown in the flowchart of FIG. 11, until the energization of the heater 26 of the oxygen concentration sensor 20 is started first after the start-up of the internal combustion engine 1, each step from step S1 to step S11 is executed according to the same procedure as that in the case of the heater control device according to the first embodiment. Here, description will be begun from a state where in step S6, the heater release status is turned on and thus the energization of the heater 26 is started.

If the energization of the heater 26 is started in step S6, in step S51, whether or not the internal combustion engine 1 has entered the automatically stopped state by the idle stop control is determined. In a case where the internal combustion engine 1 has not entered the automatically stopped state (a case of No), the determination of step S51 is repeated until the automatically stopped state of the internal combustion engine 1 by the idle stop control is created.

On the other hand, if the internal combustion engine 1 enters the automatically stopped state by the idle stop control, the routine proceeds to step S52, and determination of whether or not heater release may be continued is started.

FIG. 12 is a flowchart showing an example of a method of determining continuation of the heater release. In this example, first, in step S61, whether or not the model temperature Tmdl is greater than or equal to the integration start threshold value Tmdl_thre is determined. Although not appear in the flowchart, the model temperature Tmdl is continuously calculated along the procedure of step S21 to step S22 of FIG. 7. In a case where the model temperature Tmdl is greater than or equal to the integration start threshold value Tmdl_thre (a case of Yes), the routine proceeds to step S62, and now, whether or not the duration of the automatic stop of the internal combustion engine 1 by the idle stop control is less than the correction release threshold value is determined.

In a case where the duration is less than the correction release threshold value (a case of Yes), since there is no concern that condensed water may be generated at the installation position of the oxygen concentration sensor 20, the routine proceeds to step S63, and it is determined that the energization of the heater 26 may be continued, and the heater release continuation determination is ended and the routine proceeds to step S53.

On the other hand, in a case where the model temperature Tmdl is less than the integration start threshold value Tmdl_thre (a case of No) in step S61 or in a case where the duration of the automatic stop of the internal combustion engine 1 is greater than or equal to the correction release threshold value (a case of No) in step S62, since the ambient temperature of the installation position of the oxygen concentration sensor 20 is lowered and thus there is a concern that condensed water may be generated, the routine proceeds to step S64 and it is determined that the energization of the heater 26 cannot be continued, and the heater release continuation determination is ended, and the routine proceeds to step S53. At this time, the heater release status is turned off, and the heat amount correction amount and the energization start threshold value $\Sigma H\_thre$ that is set currently are also reset.

Returning back to FIG. 12, after the heater release continuation determination is performed in step S52, in step S53, whether or not the restart condition is established is determined. If the restart condition is not established (in a case of No), the routine returns back to step S52, and the heater release continuation determination is repeated until the restart condition is established.

Then, in a case where the restart condition is established (a case of Yes) in step S53, the routine proceeds to step S54, and whether or not the heater release status is turned on is determined. In a case where the heater release status is turned on, the routine returns back to step S51, and step S51 to step S54 are repeated along the procedure up to this.

On the other hand, in a case where the heater release status is turned off (a case of No) in step S54, the routine returns back to step S3, and the energization of the heater 26 is appropriately started, and each of the subsequent steps is performed so as not to generate cracks in the element due to adhesion of the condensed water.

As described above, in the heater control device of an oxygen concentration sensor according to the second embodiment, even in a case where the automatic stop and the restart of the internal combustion engine 1 by the idle stop control are repeated after the start-up of the internal combustion engine 1, it is possible to start the energization of the heater 26 at an appropriate time, and thus it is possible to obtain the same effect as that in the case of the heater control device of an oxygen concentration sensor according to the first embodiment.

Further, according to the heater control device of an oxygen concentration sensor related to the second embodiment, even after the energization of the heater 26 is started first, the energization of the heater 26 is stopped in consideration of the ambient temperature of the installation position of the oxygen concentration sensor 20 during the automatic stop of the internal combustion engine 1 by the idle stop control. Therefore, it is possible to prevent cracks in the element of the oxygen concentration sensor 20 from occurring due to the influence of the automatic stop of the internal combustion engine 1 by the subsequent idle stop control even though the energization of the heater 26 has been started at an appropriate time.

The heater control devices of an oxygen concentration sensor according to the first and second embodiments described above are to show an aspect of the invention and are not intended to limit the invention, and the respective embodiments can be arbitrarily changed within the scope of the invention. The heater control devices of an oxygen concentration sensor according to the first and second embodiments can be changed as follows, for example.

(1) Each constituent element configuring the exhaust system of the internal combustion engine described in the first and second embodiments or the setting values and the setting conditions of the electronic control device 30 are absolutely an example and can be arbitrarily changed.

(2) The heater control devices of an oxygen concentration sensor according to the first and second embodiments add the heat amount correction amount during the automatic stop of the internal combustion engine 1 by the idle stop control to the energization start threshold value $\Sigma H\_thre$. However, a configuration may be made so as to subtract the heat amount correction amount from the integrated heat amount $\Sigma H$. Also by performing correction in this manner, it is possible to start the energization of the heater 26 at an appropriate time. At this time, by providing the lower limit in the integrated heat amount $\Sigma H$, like providing the upper limit in the energization start threshold value $\Sigma H\_thre$, the energization start time is prevented from being determined to deviate from an actual condensed water generation status, and thus it is possible to prevent delay of the start of energization of the heater 26.

(3) The heater control devices of an oxygen concentration sensor according to the first and second embodiments reset the model temperature Tmdl, the energization start threshold value $\Sigma H\_thre$, and the heat amount correction amount, at the time of the next start-up of the internal combustion engine 1, when the internal combustion engine 1 is stopped, without depending on the idle stop control. However, a configuration may be made so as to perform the reset at the time of stop of the internal combustion engine 1.

(4) The heater control devices of an oxygen concentration sensor according to the first and second embodiments integrate the heat amount correction amount during the automatic stop of the internal combustion engine 1 by the idle stop control and add the obtained value to the energization start threshold value $\Sigma H\_thre$ at the time of the restart. However, a configuration may be made so as to add the obtained value to the energization start threshold value $\Sigma H\_thre$ at any time during the automatic stop.

(5) The heater control devices of an oxygen concentration sensor according to the first and second embodiments incorporate the influence of disturbance that is not reflected in the calculation of heat amount balance, into the integration start threshold value Tmdl_thre which becomes a threshold value of whether or not the integration of the amount of heat is started. However, a configuration may be made so as to incorporate the influence of disturbance into the energization start threshold value $\Sigma H\_thre$.

The invention claimed is:

1. A heater control device of an oxygen concentration sensor, which is provided in an exhaust pipe of an internal combustion engine capable of executing idle stop control to automatically stop the internal combustion engine during temporary stop of a vehicle and includes a sensor element that detects oxygen concentration in exhaust gas and a heater that heats the sensor element, the heater control device controlling energization of the heater in the oxygen concentration sensor and comprising:
- a model temperature calculator that calculates model temperature of an installation position of the oxygen concentration sensor;
- a heat amount integrator that calculates an integrated heat amount by integrating the amount of heat passing through the installation position of the oxygen concentration sensor;
- an energization instructor that starts the energization of the heater when the integrated heat amount has reached a predetermined energization start threshold value;
- a resetter that resets the integrated heat amount and the energization start threshold value at the time of stop or the time of start-up of the internal combustion engine and, on the other hand, does not reset the integrated heat amount and the energization start threshold value at the time of automatic stop and the time of restart of the internal combustion engine by the idle stop control; and
- a corrector that corrects a parameter in consideration of the influence of heat radiation during the automatic stop of the internal combustion engine by the idle stop control.

2. The heater control device of an oxygen concentration sensor according to claim 1, wherein the heat amount integrator starts integration of the amount of heat when the model temperature has reached a predetermined integration start threshold value.

3. The heater control device of an oxygen concentration sensor according to claim 2, wherein the model temperature calculator calculates the model temperature on the basis of a heat amount balance at the installation position of the oxygen concentration sensor and sets the integration start threshold value in consideration of a decrease in temperature due to the influence of disturbance in advance.

4. The heater control device of an oxygen concentration sensor according to claim 3, wherein the corrector performs the correction in consideration of the influence of heat radiation in a period of time when assumed temperature of the installation position of the oxygen concentration sensor during the automatic stop of the internal combustion engine by the idle stop control falls below assumed temperature in an idle state of the internal combustion engine.

5. The heater control device of an oxygen concentration sensor according to claim 3, wherein the corrector performs the correction in consideration of the influence of heat radiation in a period of time after the model temperature has become less than a predetermined required correction threshold value, after the automatic stop of the internal combustion engine by the idle stop control.

6. The heater control device of an oxygen concentration sensor according to claim 4, wherein the corrector seeks a difference between the assumed temperature in the idle state of the internal combustion engine and the assumed temperature during the automatic stop of the internal combustion engine by the idle stop control and subtracts the amount of heat equivalent to the difference from the integrated heat amount.

7. The heater control device of an oxygen concentration sensor according to claim 6, wherein the corrector integrates the amount of heat equivalent to the difference during the automatic stop of the internal combustion engine by the idle stop control and subtracts an integrated value of the amount of heat from the integrated heat amount at the time of restart of the internal combustion engine.

8. The heater control device of an oxygen concentration sensor according to claim 1, wherein during the automatic stop of the internal combustion engine by the idle stop control, when a duration of the automatic stop has become greater than or equal to a predetermined correction release threshold value or when the model temperature has become less than the integration start threshold value, the corrector ceases calculation of a correction amount and resets a correction amount already reflected.

9. The heater control device of an oxygen concentration sensor according to claim 1, wherein the corrector stops the subsequent correction when the integrated heat amount after the correction has fallen below a predetermined lower limit.

10. The heater control device of an oxygen concentration sensor according to claim 1, wherein the parameter is the integrated heat amount.

11. The heater control device of an oxygen concentration sensor according to claim 1, wherein the parameter is the energization start threshold value.

12. The heater control device of an oxygen concentration sensor according to claim 4, wherein the corrector seeks a difference between the assumed temperature in the idle state of the internal combustion engine and the assumed temperature during the automatic stop of the internal combustion engine by the idle stop control and adds the amount of heat equivalent to the difference to the energization start threshold value.

13. The heater control device of an oxygen concentration sensor according to claim 6, wherein the corrector integrates the amount of heat equivalent to the difference during the automatic stop of the internal combustion engine by the idle stop control and adds the integrated value of the amount of heat to the energization start threshold value at the time of restart of the internal combustion engine.

14. The heater control device of an oxygen concentration sensor according to claim 1, wherein the corrector stops the subsequent correction when the energization start threshold value after the correction has reached a predetermined upper limit.

* * * * *